(12) United States Patent
Nanushyan et al.

(10) Patent No.: US 6,432,137 B1
(45) Date of Patent: Aug. 13, 2002

(54) HIGH REFRACTIVE INDEX SILICONE FOR USE IN INTRAOCULAR LENSES

(75) Inventors: Sergei R. Nanushyan, Moscow (RU); Igor Valunin, Laguna Niguel, CA (US); Elena J. Alexeeva, Moscow (RU)

(73) Assignee: Medennium, Inc., Irvine, CA (US)

( * ) Notice: Subject to any disclaimer, the term of this patent is extended or adjusted under 35 U.S.C. 154(b) by 0 days.

(21) Appl. No.: 09/656,290

(22) Filed: Sep. 7, 2000

Related U.S. Application Data

(60) Provisional application No. 60/152,870, filed on Sep. 8, 1999.

(51) Int. Cl.$^7$ .................................................. A61F 2/16
(52) U.S. Cl. .................... 623/6.11; 525/478; 528/31; 528/43; 528/32; 623/4.1; 556/458
(58) Field of Search .......................... 525/478; 528/31, 528/43, 32; 623/6.11, 4.1; 556/458

(56) References Cited

U.S. PATENT DOCUMENTS

| | | | | |
|---|---|---|---|---|
| 3,188,299 | A | 6/1965 | Chalk | 260/46.5 |
| 3,188,300 | A | 6/1965 | Chalk | 260/46.5 |
| 3,192,181 | A | 6/1965 | Moore | 260/46.5 |
| 3,213,058 | A | 10/1965 | Boyle et al. | 260/47 |
| 3,341,490 | A | 9/1967 | Burdick et al. | 260/37 |
| 3,383,356 | A | 5/1968 | Nielson | 260/46.5 |
| 3,436,366 | A | 4/1969 | Modic | 260/37 |
| 3,453,233 | A | 7/1969 | Flatt | 260/46.5 |
| 3,457,214 | A | 7/1969 | Modic | 260/37 |
| 3,996,187 | A | 12/1976 | Travnicek | 260/37 |
| 3,996,189 | A | 12/1976 | Travnicek | 260/37 SB |
| 4,099,859 | A | 7/1978 | Merrill | 351/160 |
| 4,120,570 | A | 10/1978 | Gaylord | 351/40 |
| 4,122,246 | A | 10/1978 | Sierawski | 528/15 |
| 4,139,513 | A | 2/1979 | Tanaka et al. | 260/29.6 TA |
| 4,139,523 | A | 2/1979 | Lohr, Jr., et al. | 260/45.75 W |
| 4,139,692 | A | 2/1979 | Tanaka et al. | 526/218 |
| 4,261,875 | A | 4/1981 | LeBoeuf | 260/29.7 H |
| 4,277,595 | A | 7/1981 | Deichert et al. | 528/26 |
| 4,304,895 | A | 12/1981 | Loshaek | 526/313 |
| 4,310,650 | A | 1/1982 | Gupta et al. | 526/313 |
| 4,410,674 | A | 10/1983 | Ivani | 526/279 |
| 4,418,165 | A | 11/1983 | Polmanteer et al. | 523/210 |
| 4,447,981 | A | 5/1984 | Bauer | 43/42.21 |
| 4,450,264 | A | 5/1984 | Cho | 526/279 |
| 4,463,149 | A | 7/1984 | Ellis | 526/279 |
| 4,507,452 | A | 3/1985 | Foley | 526/279 |
| 4,525,563 | A | 6/1985 | Shibata et al. | 526/279 |
| 4,528,311 | A | 7/1985 | Beard et al. | 524/91 |
| 4,537,943 | A | 8/1985 | Talcott | 528/15 |
| 4,542,542 | A | 9/1985 | Wright | 623/6 |
| 4,550,139 | A | 10/1985 | Arkles | 525/90 |
| 4,600,751 | A | 7/1986 | Lee et al. | 525/404 |
| 4,608,050 | A | 8/1986 | Wright et al. | 626/6 |
| 4,611,039 | A | 9/1986 | Powell et al. | 526/271 |
| 4,612,358 | A | 9/1986 | Besecke et al. | 526/259 |
| 4,615,702 | A | 10/1986 | Koziol et al. | 623/6 |
| 4,647,282 | A | 3/1987 | Fedorov et al. | 623/4 |
| 4,785,047 | A | 11/1988 | Jensen | 524/714 |
| 4,801,642 | A | 1/1989 | Janik et al. | 524/714 |
| 4,803,254 | A | 2/1989 | Dunks et al. | 525/477 |
| 4,868,251 | A | 9/1989 | Reich et al. | 525/479 |
| 4,882,398 | A | 11/1989 | Mbah | 525/478 |
| RE33,477 | E | 12/1990 | Loshaek | 526/313 |
| 5,070,169 | A | 12/1991 | Robertson et al. | 528/25 |
| 5,070,170 | A | 12/1991 | Robertson et al. | 528/25 |
| 5,077,335 | A | 12/1991 | Schwabe et al. | 524/474 |
| 5,164,462 | A | 11/1992 | Yang | 525/478 |
| 5,236,970 | A | 8/1993 | Christ et al. | 523/113 |
| 5,286,829 | A | 2/1994 | Fedorov et al. | 527/201 |
| 5,321,108 | A | 6/1994 | Kunzler et al. | 526/242 |
| 5,346,507 | A | 9/1994 | Fedorov et al. | 623/6 |
| 5,352,714 | A | 10/1994 | Lai et al. | 523/107 |
| 5,376,737 | A | 12/1994 | Yang | 525/477 |
| 5,391,590 | A | 2/1995 | Gerace et al. | 523/107 |
| 5,411,553 | A | 5/1995 | Gerace et al. | 623/6 |
| 5,444,106 | A | 8/1995 | Zhou et al. | 523/107 |
| 5,480,946 | A | 1/1996 | Mueller et al. | 525/479 |
| 5,512,609 | A | 4/1996 | Yang | 523/107 |
| 6,162,854 | A | * 12/2000 | Meguriya et al. | |

FOREIGN PATENT DOCUMENTS

| | | |
|---|---|---|
| CA | 1273144 | 8/1990 |
| EP | 110537 | 10/1983 |
| GB | 1480880 | 4/1975 |

* cited by examiner

*Primary Examiner*—Robert Dawson
*Assistant Examiner*—Kuo-Liang Peng
(74) *Attorney, Agent, or Firm*—Frost Brown Todd LLC

(57) ABSTRACT

An intraocular lens made from a class of optically clear, ultraviolet (UV) light absorbing, vulcanized silicone compositions containing about 35 mole % or greater phenyl groups ($C_6H_5$), suitable for implanting in the human eye is disclosed. The high mole percentage of phenyl groups in the vulcanized silicone compositions provides a high refractive index (at least about 1.50) and partially blocks ultraviolet light absorption. The composition is formed by the vulcanization of a mixture which comprises, for example, the following polyorganovinylsiloxane components:

Component (I): $\alpha$, $\omega$-bis(trivinylsiloxy) oligodimethyldiphenylvinylmethylsiloxane;

Component (II): $\alpha$, $\omega$-bis(trimethylsiloxy ) oligodimethyldiphenylmethylhydro-siloxane;and Component (III): $\alpha$, $\omega$-bis(trimethylsiloxy) oligomethylphenylvinylmethylphenyl-siloxane;

together with Component (IV) a polyaddition reation catalyst, particularly a complex platinum catalyst (for example, the complex of platinum and hexavinyldisiloxane); wherein the ratio, by weight, of the mixture in the four components (I:II:III:IV respectively) in the pre-vulcanized mixture is from about 0.9:0.1:0.015:0.006 to about 0.7:0.3:0.05:0.01.

13 Claims, 1 Drawing Sheet

HIGH REFRACTIVE INDEX SILICONE FOR USE IN INTRAOCULAR LENSES

This application is based on and claims priority from U.S. Provisional Application No. 60/152,870, Nanushyan and Valunin, filed Sep. 8, 1999.

BACKGROUND OF THE INVENTION

The current invention relates to high refractive index, optically clear, silicone polymers, which are used, for example, to make intraocular lenses (IOL).

Optically clear materials, such as glass, polymethylmethacrylate and cured silicone materials, are used in intraocular lenses and are currently known in the art. In order to be useful for such lenses, the materials must have a number of suitable properties including optical clarity, appropriate mechanical properties, relatively low density, resistance to discoloration, and biological compatibility for long-term implantation as a medical device. The refractive power of a lens is a function of its optic shape and the refractive index of the material from which it is made. The higher the refractive index, the thinner a lens can be made for a specified power. Thus, refractive index is a very important property for materials used to make IOL's.

The flexibility of the materials is important to permit implanting intraocular lenses through small incisions for cataract surgery. Use of a flexible material permits folding or compression of the lens and/or supporting elements, such as haptics, during or prior to insertion, to reduce the size of the incision required. A smaller ocular incision reduces trauma and permits the use of sutureless incision techniques, thus reducing the potential for distorting the shape of the eye and inducing astigmatism.

Aphakic IOLs are used for replacement of the natural lens for treatment of cataracts. Phakic IOLs are used for the correction of myopia and hyperopia where the natural lens is not removed. Posterior chamber phakic lenses have been shown to improve best spectacle corrected visual acuity over external lenses. Most cataract IOLs are implanted in the space created by surgical removal of the diseased natural lens. Posterior chamber phakic IOLs require thinner and more flexible lens construction than the traditional aphakic, cataract IOLs to permit implantation between the iris and the natural lens (that is, in the posterior chamber of the eye) where a thick or stiff lens makes it difficult to avoid disrupting the normal functions of the eye, such as accommodation (focusing) of the natural lens, constriction and dilation of the iris, and the flow of the aqueous fluid (or humor) of the eye. Soft and flexible materials are especially important for phakic IOLs to allow the implant to move with the dynamics of the anatomy. A lens made from a material with high refractive index can be thinner and provide the same refractive power as a thicker lens made from a material having a low refractive index. Thinner lenses are inherently more flexible and are more easily folded or compressed for insertion through small incisions.

Such materials as silica have been used to reinforce optically clear silicones to increase tensile and tear strength. However, silica reinforcement also increases the stiffness of the material which may not be desirable for use in phakic IOLs. Also, reinforcing materials must have the same refractive index as the base material to achieve optical clarity. For example, if a 1.50 refractive index silicone is reinforced with silica which has a refractive index 1.46, the resulting material would scatter light and not be suitable for use as a lens. Thus, the use of reinforcing materials is difficult to execute in a lens, and it would be useful to be able to formulate reliably strong, optically clear silicone materials without using reinforcing agents.

The use of multiple IOLs ("piggybacked") to achieve a specific optical power is a new technique used by surgeons where the specific required power is not available in a single lens or where a correction in power is required postoperatively. Addition of a lens to a sudophakic eye (where the natural lens has been removed and replaced with an IOL) is another application of the present invention since high refractive index, UV absorbency, and flexibility are important characteristics of such lenses.

Ultraviolet light (UV) absorbing materials are important for ocular prosthetics, such as IOLs, to avoid damage to tissues (such as the retina) from normal exposure to sunlight and other sources of UV light. Further, it is essential that such materials remain optically clear and avoid yellowing or other discoloration resulting from deposits or precipitates within the lens or on its surface. Methods for blocking UV light that are known in the art include the use of benzotriazole in the lens as an additive or as part of a copolymer.

There is, therefore, a need for an intraocular lens made from implantable materials with a high refractive index, that will absorb UV light, and provide adequate mechanical properties including a very high level of flexibility, while avoiding additives and agents that may be extractable or leachable or discolor the lens.

The current invention is useful in aphakic IOLs for the treatment of cataracts. However, the invention is particularly useful in phakic IOLs for refractive surgery. The development of phakic IOLs for the correction of myopia and hyperopia where the natural lens is not removed is described in U.S. Pat. No. 4,585,456, Blackmore, issued Apr. 29, 1986. The use of phakic IOLs has been shown to improve best spectacle corrected visual acuity (Dimitrity Dementiev M. D. and Alexander Hatsis, M. D., *Symposium on Cataract, IOL and Refractive Surgery*, Session 3-B, Apr. 26–30 1997, Boston Mass., ASCRS, Fairfax, Va.). Posterior chamber phakic IOLs require thinner and more flexible lens construction than the traditional aphakic IOLs for the treatment of cataracts where the IOL is implanted in the space created by the surgical removal of the natural lens.

Optically clear silicone materials with a relatively high refractive index are known in the art. Such materials are typically formulated by the use of additives or co-monomers in the silicone polymer material; this generally results in undesirable trade-offs in the other properties of the material, such as strength, flexibility, elasticity or elongation.

Canadian Patent 1,273,144, Nishimura, published Aug. 21, 1990, discloses the inclusion of refractive index-modifying groups, such as phenyl groups, into hydride-containing siloxanes by reacting a portion of the hydride groups with carbon- carbon unsaturated bonds in the refractive index-modifying group. After this reaction, the unreacted hydride groups in the modified hydride-containing siloxane are reacted with a compound having at least two carbon-carbon unsaturated bonds to form a cross-linked polysiloxane. This system is somewhat difficult to control and may not be suited for mass production of silicone lenses because of potentially large batch-to-batch quality variations. For example, the refractive index-modifying groups must be sufficiently numerous and evenly distributed in the hydride-containing siloxane to provide for the desired refractive index without detrimentally affecting the other properties of the final polymer. At the same time, the unreacted hydride groups remaining in the siloxane must be sufficiently numerous and evenly distributed to provide for the desired cross-linking reaction. These factors can create a reaction control problem which may result in the final polymer not having the desired refractive index and /or not having one or more other desired physical properties.

U.S. Pat. No. 4,882,398, Mbah, issued Nov. 21, 1989, discloses optically-clear silicone compounds adaptable for use in windows, windshields and lenses. Although this patent does disclose certain aryl and aralkyl groups attached or bonded to a siloxane, there is no teaching or suggestion of the effect of such substitution on the refractive index of the final polymer. Also, the amount of these groups which is included should have little or no effect on the refractive index of the final polymer and would yield a low refractive index of about 1.41. This is consistent with the fact that for many of the disclosed uses (e.g., windows, windshields), refractive index is not a critical property.

Gas permeable, wettable and hydrophilic materials are well-known in the art for use in contact lenses and other applications. Examples of such materials are disclosed in U.S. Pat. Nos. 4,099,859, Merrill, issued Jul. 11, 1978; U.S. Pat. No. 4,120,570, Gaylord, issued Oct. 17, 1978; U.S. Pat. No. 4,139,513, Tanaka, issued Mar. 20, 1978; U.S. Pat. No. 4,139,523, Tanaka, et al., issued Feb. 13, 1979; U.S. Pat. No. 4,139,692, Tanaka et al., issued Feb. 13, 1979; U.S. Pat. No. 4,261,875, Le Boeuf, issued Apr. 18, 1981; U.S. Pat. No. 4,277,595, Deichert et al., issued Jul. 7, 1981; U.S. Pat. No. 4,410,674, Ivani, issued Oct. 18, 1983; U.S. Pat. No. 4,447,981, Arkles, issued Oct. 23, 1984; U.S. Pat. No. 4,507,452, Foley; issued Mar. 26, 1985; U.S. Pat. No. 4,450,264, Choyce, issued May 22, 1982; U.S. Pat. No. 4,463,149, Ellis, issued Jul. 31, 1984; U.S. Pat. No. 4,550,139, Arkels, issued Oct. 29, 1985; U.S. Pat. No. 4,525,563 Shibata et al., issued Jun. 25, 1985; U.S. Pat. No. 4,600,751, Lee et al., issued July 15, 1986; U.S. Pat. No. 4,611,039, Powell et al., issued Sep. 9, 1986; U.S. Pat. No. 5,070,169, Robertson, et al., issued Dec. 3, 1991; U.S. Pat. No. 5,070,170, Robertson et al., issued Dec. 3, 1991; U.S. Pat. No. 5,321,108, Kunzler et al., issued Jun. 14, 1984; U.S. Pat. No. 5,352,714, Lai et al., issued Oct. 4, 1994; U.S. Pat. No. 5,480,946, Mueller, et al., issued Jan. 2, 1996; U.S. Pat. No. 5,346,507, Fedorov et al., issued Sep. 13, 1994; U.S. Pat. No. 5,286,829, Fedorov et al., issued Feb. 15, 1994; and in British Patent 1,480,880, issued Jul. 27, 1977. A hydrophilic material is not desirable for a permanently implanted prosthetic device, such as an IOL, where it is necessary to avoid the eventual discoloration from precipitates that can enter and form deposits within the material or on the surface of the lens.

Inhibitors are used in many silicones to facilitate the manufacturing process by enabling storage of premixed components prior to the polymerization. U.S. Pat. No. 3,436,366, Modic, issued Apr. 1, 1969, discloses filled silicone compositions that do not use an inhibitor but must be stored at 0° C. Such storage requirements complicate the manufacture of the material. U.S. Pat. No. 3,188,299, Chalk, issued Jun. 8, 1965, and U.S. Pat. No. 3,188,300, Chalk, issued Jun. 8, 1965, disclose the preparation of silicones in the presence of nitrogen-containing or phosphorous-containing ligands for reducing the activity of a platinum catalyst. U.S. Pat. No. 3,192,181, Moore, issued Jun. 29, 1965, describes an optically clear silicone proposed for use in contact lenses and containing volatile inhibitors to permit storage in sealed containers. In U.S. Pat. No. 3,383,356, Nelson, issued May 14, 1968, it is taught that volatile halocarbon catalyst inhibitor additives can be used in reactive organosilicone compositions for inhibiting polymerzation. U.S. Pat. No. 3,453,233, Flatt, issued Jul. 1, 1969, discloses a mixture of inhibitor and crosslinker compounds. U.S. Pat. No. 4,801,642, Janik, issued Jan. 31, 1989, discloses contact lenses containing hydrophilic silicone polymers with inhibitors containing amines to permit long-term storage. U.S. Pat. No. 5,077,335, Schwabe et al., issued Dec. 31, 1991, discloses an optically-clear silicone which contains inhibitors. Inhibitors taught in the art may be convenient to use in the manufacturing process, but can result in materials which are less biocompatable than non-inhibited compositions because the inhibiting compound may be extractable or add to the potential for release of free radicals from the polymerized composition.

One group of materials known in the art that does not use inhibitors is low temperature vulcanizing (LTV), in situ curing silicones that are injected into the empty capsule of the eye following extraction of the natural lens. Examples of these materials and lenses made from them are disclosed in U.S. Pat. Nos.: 4,122, 246, Sierawski, issued Oct. 24, 1978; U.S. Pat. No. 4,542,542, Wright et al., issued Sep. 24, 1985; U.S. Pat. No. 4,608,050, Wright et al., issued Aug. 26, 1986; U.S. Pat. No. 4,537,943, Talcott, issued Aug. 27, 1985; U.S. Pat. No. 5,391,590, Gerace, issued Feb. 21, 1995; and U.S. Pat. No. 5,411,553, Gerace, issued May 2, 1995 issued. These materials are specifically designed to vulcanize at body temperature and avoid the use of inhibitors by being mixed just prior to use.

Optically clear silicone polymers reinforced by adding silica to improve mechanical properties are well known in the art. Silica reinforced materials are disclosed in the following U.S. Pat. No.: 3,341,490, Burdick, issued Sep. 12, 1967; U.S. Pat. No. 3,383,356, Nelson, et al., issued May 14, 1968; U.S. Pat. No. 3,457,214, Modic, issued Jul. 22, 1969; U.S. Pat. No. 3,996,187, Modic, issued Dec. 7, 1976; U.S. Pat. No. 3,996,189, Modic, issued Dec. 7, 1976; U.S. Pat. No. 4,418,165, Travnicek, issued Nov. 11, 1983; U.S. Pat. No. 4,615,702, Polmanteer et al.; issued Oct. 7, 1986; U.S. Pat. No. 4,785,047, Koziol, issued Nov. 15, 1988; U.S. Pat. No. 4,882,398, Mbah, issued Nov. 21, 1989; U.S. Pat. No. 5,236,970, Christ, issued Aug. 17, 1993; U.S. Pat. No. 5,444,106 Zhou, issued Aug. 22, 1995; U.S. Pat. No. 5,494,946, Christ, issued May 30, 1995; and European Application 110537, Ulman, et al. published Jun. 13, 1984. These compositions have the advantage of higher resilience, tear and tensile strength, but they also have the disadvantage of greater stiffness due to reinforcement by the silica. Reinforcing with silica also limits the potential for increasing the refractive index beyond 1.46 (the refractive index of silica). If the refractive index of the polymer and the reinforcing material are different, the interface between the two materials will cause light scattering and the final product will appear milky. Therefore, high refractive index materials for IOLs are preferably made without reinforcing materials, such as silica.

The materials of the present invention and the IOLs made from those materials, are unique in that they:

1. are optically clear and flexible with a refractive index of about 1.50 or greater;
2. have adequate tear and tensile strength that will permit compression for insertion through a small incision or for folding prior to insertion;
3. have adequate resilience for the IOL to return to its original shape following insertion; and
4. have sufficient flexibility to cope with the dynamic movement of the surrounding anatomy after implantation or to permit surgical removal of the device through a small incision at a later date.

In addition, the materials do not discolor, do not require the use of silica reinforcing materials, are biocompatible, and, very unexpectedly, are UV light absorbing.

Ultraviolet (UV) light (wavelength from about 200 to 400 nanometers) absorbing materials are important for ocular prosthetics, such as IOLs, to avoid damage to tissues, such as the retina, from normal exposure to sunlight and other sources of UV. It has become standard practice to add UV stabilizers to light sensitive polymers and to add UV absorbing compounds to corrective lenses (such as eye glasses or IOLs). UV-B rays, in the wave length range of 280 to 320 nanometers, are the most damaging. Means for achieving UV absorbing materials are known in the art. U.S. Pat. No. 3,213,058, Boyle, issued Oct. 19, 1965, discloses a class of optically clear, ultraviolet (UV) light absorbing, vulcanized silicone compositions for use in implantable, medical prosthetic devices, such as intraocular lenses. UV absorbing compounds are incorporated in the material via reaction with carboxy and hydroxy groups contained in silicone compounds. U.S. Pat. No. 4,304,895 (Re33,477), Loshaek, issued Dec. 8, 1981, discloses copolymers for use in hard contact lenses containing benzophenone derivatives that are in steady state with respect to extraction from the lens in an aqueous medium. More specifically, Loshaek discloses the use of 2-hydroxy-4-methacryloxybenzophenone and mixtures thereof as an ultraviolet light absorber that is copolymerizable with acrylic monomers to yield hard contact lenses materials. U.S. Pat. No. 4,310,650, Gupta et al., issued Jan. 12, 1982, discloses copolymerization of an allyl-2-hydroxy-benzophenone with an acrylic ester, such as polymethylmethacrylate for absorbing UV. U.S. Pat. No. 4,528,311, Beard et al., issued Jul. 9, 1985, discloses certain benzotriazole monomers which are copolymerizable with vinyl monomers, such as polymethylmethacrylate, to yield UV absorbing optically clear polymers. U.S. Pat. No. 4,612,358 Besecke et al., issued Sep. 16, 1986, discloses alkyl groups and cyclic groups in compounds susceptible to free-radical polymerization for absorbing UV light. U.S. Pat. No. 4,868,251, Reich, issued Sep. 19, 1989, and U.S. Pat. No. 5,164,462, Yang, issued Nov. 17, 1992, teach the use of alkoxy radicals and halogen groups with a terminal double bond or alkyl radicals to achieve UV absorbency. In U.S. Pat. No. 4,803,254, Dunks, issued Feb. 7, 1989, are taught UV absorbing compositions containing benzotriazole, as well as the use of vinylsilylalkoxy arylbenzotriazole to yield additives that absorb over 90% of the UV light. The compounds are said to be compatible with silicone polymers and can be incorporated into silicone polymers through covalent bonding to impart the UV absorbing properties. Dunks discloses that his materials have a low level of extractables which he achieves by maximizing bonding with the base polymer. U.S. Pat. No. 5,346,507, Fedorov, issued Sep. 13, 1994, discloses UV absorbing compounds for PMMA that are not used for silicones. U.S. Pat. No. 5,376,737, Yang, issued Dec. 27, 1994, discloses a method for introducing a UV absorbing material into a vulcanized solid material such that it is cross-linked or reacted with the improved material and the UV absorbing material cannot be extracted. U.S. Pat. No. 5,444,106, Zhou, issued Aug. 22, 1995, discloses high refractive index silicone compositions for IOLs containing a silica filler and a combination UV absorber and cross-linking reagent. Typically, phenyl chromophores (as used in the present invention) do not absorb light with a wavelength above 300 nm and, therefore, are not known as UV absorbers.

U.S. Pat. No. 4,647,282, Fedorov, et al., issued Mar. 3,1987, discloses materials and methods used to manufacture optical prosthetic devices by polymerization of a mixture of:

A: $\alpha,\omega$-bis-trivinylsilyloligodimethyl(methylphenyl)-siloxane, and

B: $\alpha,\omega$-bis-methyldimethylhydrosiloxyoligomethyl (phenyl)methylhydro-siloxane, in the presence of a platinum polyaddition reaction catalyst where the ratio of A:B in said mixture is from 100:1 to 100:20 parts by weight. The resulting vulcanized material contains about 12 to 18% phenyl groups and has a refractive index up to 1.48. These non-reinforced materials were successfully biocompatibility and toxicity tested, and IOLs made from these materials were successfully implanted in hundreds of patients (A. V. Tereschenko et al., Ocular Surgery News, 1996, and Dimitrity Dementiev, M. D. and Alexander Hatsis, M. D.; *Symposium on Cataract, IOL and Refractive Surgery*, Session 3-B, Apr. 26–30 1997, Boston, Mass., ASCRS, Fairfax, Va.). The patent teaches that if the ratio of the A:B mixture is less than about 100:1, the strength of the material is reduced so that it cannot be implanted in the eye without deformation. Also, if said ratio is greater than 100:20, the stiffness achieved is such that a lens made from such material is difficult to insert. Ultraviolet (UV) light transmission for the disclosed materials is 85% to 95%.

U.S. Pat. No. 5,512,609, Yang, issued Apr. 30, 1996, describes high refractive index, siloxane-based, cross-linked polymers which are useful in producing foldable intraocular lenses. The patent teaches that the aryl-containing siloxanes preferably comprise at least about 20% or more of the total silicone-bound substituents.

The prior art does not fully satisfy the need for a very flexible intraocular lens having UV absorbency, excellent biocompatibility, and high refractive index to permit a sufficiently thin lens for some aphakic, sudophakic, and phakic applications. It is, therefore, an object of the present invention to provide IOLs which are optically clear, have a high refractive index (at least about 1.50) to provide thinner lenses with reduced mass, that are UV absorbing, have adequate mechanical properties to withstand folding or compression for insertion through a small incision, have high elasticity and are biocompatible without the use of UV absorbers (such as benzotriazole), reinforcing materials, fillers, or inhibitors.

SUMMARY OF THE INVENTION

The present invention is an intraocular lens made from a class of optically clear, ultraviolet (UV) light absorbing, vulcanized silicone compositions having a content of phenyl groups (as used herein, the term "phenyl" is intended to encompass both unsubstituted and substituted (which are technically "aryl") groups) of at least about 35 mole % (and preferably at least about 45 mole %), suitable for implanting in the human eye, particularly for use as a phakic lens located in the posterior chamber of the eye. The high mole percentage of phenyl groups in the vulcanized silicone compositions (the vulcanizate) provides a high refractive index (at least about 1.50) and blocks ultraviolet light which can damage the natural lens or the retina. The silicone compositions comprise a polymerized mixture of three polyorganovinyl-siloxane components:

Component I: $\alpha,\omega$-bis(trivinylsiloxy) oligodimethyl-diphenylvinylmethylsiloxane;

Component II: $\alpha,\omega$-bis(trimethylsiloxy) oligodimethyl-diphenylmethylhydrosiloxane; and Component III: $\alpha,\omega$-bis(trimethylsiloxy) oligomethylphenylvinylmethylphenyl-siloxane;

which are combined together with

Component IV: a complex polyaddition catalyst (preferably a compound of platinum and hexavinyldisiloxane).

In these silicone component mixtures, the ratio of the four components (I:II:III:IV respectively) ranges from about 0.9:0.1:0.015:0.006 to about 0.7:0.3:0.05:0.01 parts by weight (i.e., Component I may vary from about 0.7 to 0.9 weight parts; Component II from about 0.1 to about 0.3 weight parts; Component III from about 0.015 to about 0.05 weight parts; and Component IV from about 0.006 to about 0.01 weight parts).

DETAILED DESCRIPTION OF THE INVENTION

Figure 1:
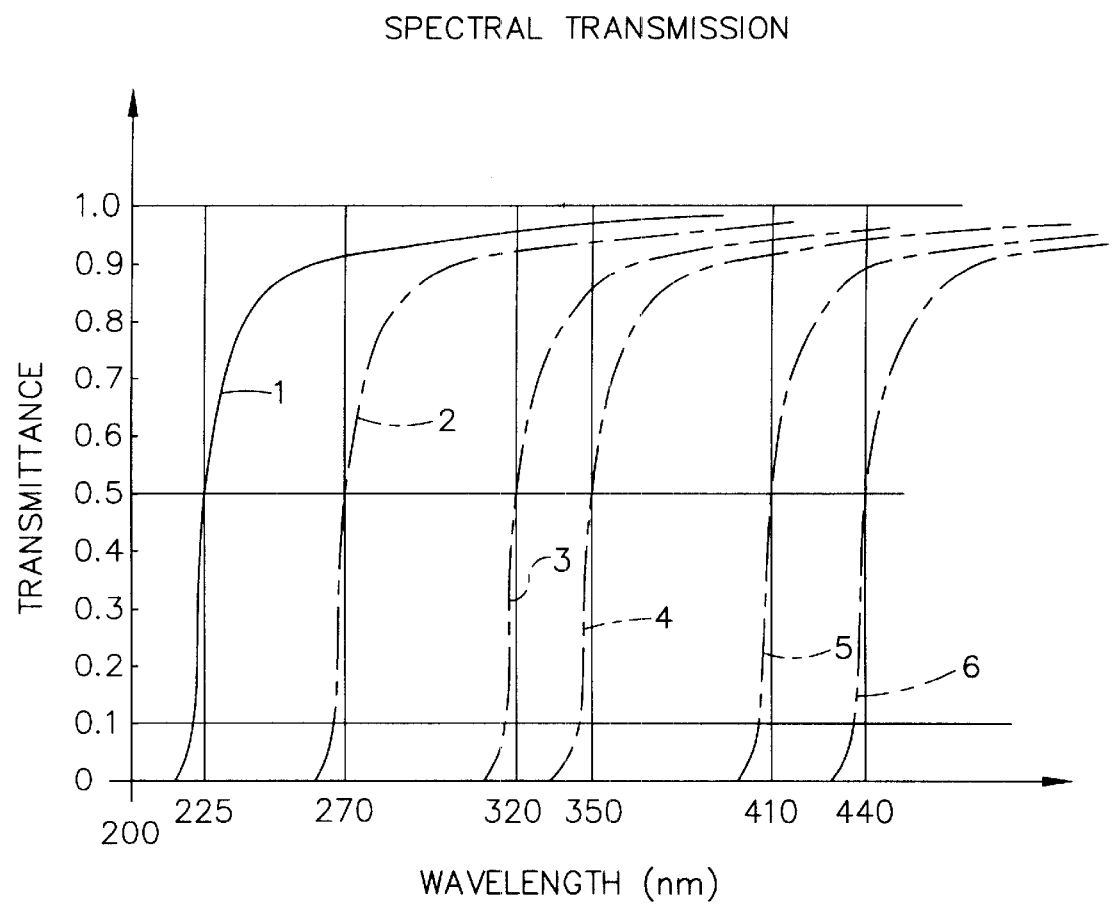
FIG. 1 shows the UV absorption ability of the silicone materials of the present invention, as well as a control material.

The current invention relates to a class of intraocular lenses (IOLs) which comprise an optic or light transmitting means and other functional means such as supporting means or haptics, where the optic or light transmitting means is made of a specifically-defined flexible silicone organic material. The materials described herein are particularly useful in constructing the IOLs described in PCT Published Application WO98/17205, Valunin, et al., published Apr. 30, 1998, incorporated herein by reference. Said silicone organic material differs from prior materials known in the art in that it contains about 35 mole % or greater phenyl groups (preferably at least about 45 mole %, most preferably from about 45 to about 65 mole %) and possesses the following properties without including additives, fillers, or inhibitors that may lower the biocompatibility or flexibility of the finished lens:

1. A refractive index of at least about 1.50, preferably at least about 1.52, most preferably at least about 1.54, to permit the lens to be thin such that it will easily fit within the anatomy of the eye (such as the posterior chamber between the iris and natural lens) and can be folded or compressed for insertion through a small, suture-less incision to reduce the risk of induced astigmatism.
2. The ability to absorb at least about 50% of ultraviolet (UV) light, which is normally defined as light having a wavelength of between about 200 and 400 nanometers, to reduce the potential of trauma to tissue of the eye. In particular, UV-B light, which is in the wavelength range of from about 280 to about 320 nanometers, is the most dangerous to the natural lens and retina of the eye.
3. Mechanical properties that will:
   permit folding and injection of the lens through a small incision
   provide resilience such that the optic can maintain its shape for proper optical refraction without distortion
   allow molding of a variety of flexible lens designs, such as a one- piece lens with both optic and support means (such as a haptic) that is flexible and which can move with the normal movement of the anatomy such as dilation and constriction of the iris, accommodation (focusing by change of radius) of the natural lens, and flow of the aqueous humor within the eye.

Said silicone organic material is made from a composition which is created by polymerization of a mixture the three compositions with the following general chemical formulas; together with a polyaddition reaction catalyst.

Formula for Component I-Polyorganovinylsiloxane (POS):

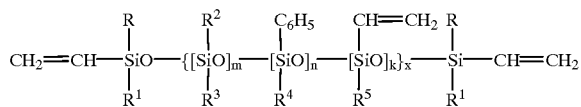

Where: $m+n+k=1$; $m$=about 0.29 to about 0.70; $n$=about 0.30 to about 0.70; $k$=0 to about 0.03; $x$=about 90 to about 450, and R and $R^1$ are selected from $C_1$–$C_4$ alkyl, $C_1$–$C_4$ alkenyl and $C_6H_5$, preferably (CH=$CH_2$), but R and $R^1$ may also preferably be $CH_3$ or $C_6H_5$ $R^2$ and $R^3$ are selected from $C_1$–$C_4$ alkyl and $C_6H_5$, preferably $CH_3$, but $R^2$ and $R^3$ may also preferably be $C_2H_5$ or $C_6H_5$ $R^4$ is selected from $C_1$–$C_4$ alkyl and $C_6H_5$, preferably $C_6H_5$, but may also preferably be $CH_3$ $R^5$ is selected from $C_1$–$C_4$ alkyl and $C_6H_5$, preferably $CH_3$, but may also be $C_6H_5$ In a preferred embodiment, Component I has the formula $$(CH=CH_2)_3SiO\{[(CH_3)_2SiO]_m[(C_6H_5)_2SiO]_n[CH_3(CH_2CH)SiO]_k\}_xSi(CH=CH_2)_3$$

wherein $m+n+k=1$, m is from about 0.5 to about 0.7, n is from about 0.3 to about 0.5, k is from about 0.01 to about 0.02, and x is from about 350 to about 450.

Formula for Component II—Hydride Oligomer (HO):

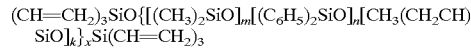

Where: $a+b+c=1$; $a$=about 0.2 to about 0.7; $b$=about 0.2 to about 0.4; $c$=0 (preferably 0.01) to about 0.04; $y$=about 5 to about 22, and $R^6$ is selected from $C_1$–$C_4$ alkyl and $C_6H_5$, preferably $CH_3$, or $C_6H_5$, but may also preferably be $C_2H_5$ $R^7$ is selected from $C_1$–$C_4$ alkyl and $C_6H_5$, preferably $C_6H_5$, but may also preferably be $CH_3$, $C_2H_5$, or $C_3H_7$ $R^8$ is selected from $C_1$–$C_4$ alkyl and $C_6H_5$, preferably $CH_3$ or $C_6H_5$, but may also preferably be $C_2H_5$ $R^9$ is selected from $C_1$–$C_4$ alkyl and $C_6H_5$, preferably $C_6H_5$, but may also preferably be $CH_3$, $C_2H_5$, or $C_4H_9$ In a preferred embodiment, Component II has the formula

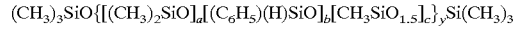

wherein $a+b+c=1$, a is from about 0.4 to about 0.5, b is from about 0.2 to about 0.4, c is from about 0.02 to about 0.04, and y is from about 5 to about 10.

Formula for Component III—an adding agent, which is a "Mirror" of formula II:

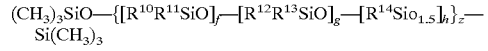

Where: $f+g+h=1$; $f$=about 0.2 to about 0.7; $g$=about 0.2 to about 0.4; $h$=0 (preferably about 0.01) to about 0.04; $z$=about 10 to about 22, and $R^{10}$, $R^{10}$, and $R^{12}$ are selected from $C_1$–$C_4$ alkyl and $C_6H_5$, with $CH_3$, $C_2H_5$ and $C_6H_5$ being preferred $R^{13}$ is $(CH=CH_2)$ $R^{14}$ is selected from $C_1$–$C_4$ alkyl, $C_1$–$C_4$ alkenyl and $C_6H_5$, preferably $(CH=CH_2)$, but may also preferably be $CH_3$, $C_6H_5$, or $C_4H_9$ The components described above are reacted in the presence of a polyaddition catalyst, preferably a platinum-containing polyaddition catalyst. A preferred catalyst is described below.

Formula for Component IV—A Preferred Catalyst is an Adduct of Platinum and a Disiloxane Having the Following Structure

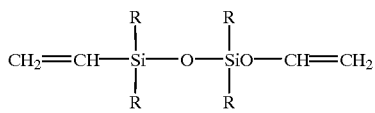

Where: R is $C_1$–$C_4$ alkyl or $C_1$–$C_4$ alkenyl, and is preferably $CH_3$ or $CH=CH_2$. When all of the R groups are $CH=CH_2$, the compound is hexavinyldisiloxane (V6) a particularly preferred catalyst.

The four components (I: II: III: IV respectively) are mixed together in the ranges from about 0.9 : 0.1 : 0.015 : 0.006 to about 0.7 : 0.3 : 0.05:0.01 parts by weight. This mixture will typically contain from about 0.7 to about 0.9 parts of component I, from about 0.1 to about 0.3 parts of component II, from about 0.015 to about 0.05 of component III, and from about 0.006 to about 0.01 of the reaction catalyst. The prevulcanized material is then placed in a mold and vulcanized at a temperature of from about 75° C. to about 150° C. to achieve the desired level of polymerization.

In general terms, the silicone material of the present invention is made by vulcanizing a mixture of two mirrored siloxane components and the vinylsiloxane, which have essentially the same refractive index, in the presence of a catalyst. These siloxane components do not differ substantially except that one contains primarily hydride substituents and the other contains primarily vinyl substituents. Each of the components, and hence the final material, has a refractive index of at least about 1.50, and the final material contains at least 35 mole %, preferably at least about 45 mole %, phenyl groups.

Extensive empirical work was required to develop the silicone component compositions and then the optimal proportional relationship to achieve a refractive index as high as 1.56, or even higher, in combination with biocompatibility of the polymerized IOL. It was discovered that exceeding the stated limits for Component I of more than 90 mass parts (out of 100) will decrease the mechanical strength of the IOL such that it cannot be folded or compressed for implantation through a small incision without distortion or damage of the shape. Using less than 70 mass parts of Component I will make the lens stiff, creating difficulty in compression for insertion during the surgical procedure and providing difficulty in flexing with the movement of the eye; in addition, the cured lens may adhere to the mold, complicating methods for its manufacture.

The appropriate length of the polymerization process should be tailored to provide a level of polymerization that avoids adhesion to the mold and yields a biocompatible cross-linked composition. Molds may be manufactured from stainless steel and other hard alloys, cultured sapphire, glass and even polymeric materials, such as polyether amides. Different mold materials require different lengths of time for the polymerization process due mostly to the variation in speed of heat transfer. Polymerization at a temperature of from about 75° C. (preferably I 110° C.) to about 150° C. for about 2 to about 10 minutes following stabilization of the temperature will generally achieve the stated goals.

Inhibitors are preferably not used as a means for control of the polymerization reaction because such inhibitors could be a source of free radicals that are leachable or extractable. Such compounds could potentially create biocompatibility issues. The silicone materials of the present invention are, therefore, substantially free from polymerization inhibitors, including, for example, various ligands and catalyst inhibitors. The silicone materials are also substantially free from silica reinforcing materials. The present invention does not require inhibitors since it is stable at below room temperature when partially mixed. A mixture of components I and II is stable when no catalyst is added. Component II is non-reactive, and when mixed with the catalyst is stable at or below room temperature. The two stable components are mixed as they are needed in the manufacturing process and remain stable at low temperatures between 0° and about 30° C. for at least about 14 hours. The mixture may also be stored at temperatures of below freezing for over 48 hours.

The polymerized vulcanizate has an absorption spectrum as illustrated in FIG. 1. Reducing the transmission of UV light reduces the potential for trauma to the retina and other tissue of the eye. The amount of UV light absorbed is dependent upon the concentration of phenyl groups in the material. This is illustrated in FIG. 1, as interpreted in the following table:

TABLE 1

| Curve # | Refractive Index ($nD^{20}$) | % (Molar)Phenyl Groups | Approximate highest wavelength absorbed (nanometers) |
|---|---|---|---|
| 1 | 1.40 | 0% | 225 nm |
| 2 | 1.46 | 25% | 270 nm |
| 3 | 1.49 | 35% | 320 nm |
| 4 | 1.52 | 45% | 350 nm |
| 5 | 1.56 | 58% | 410 nm |
| 6 | 1.60 | 65% | 440 nm |

The materials illustrated in this figure were prepared as described in the present application. The solid curve (1) in FIG. 1 represents a conventional optically clear silicone at a baseline value at about 225 nm (see table above). In the current invention, UV absorbency is a function of the concentration of phenyl groups and wavelength. Dashed line curves (2 through 6) are examples of the current invention at various concentrations of phenyl groups. This family of curves permits selection of the desired properties of the material to block UV radiation. For example, to block UV-B radiation in the range of 280 to 320 nanometers, a concentration of about 35% or greater phenyl groups would be selected. The fact that increasing the percentage of phenyl groups in the materials defined herein increases the UV absorption cut-off of the material is particularly surprising since, typically, a phenyl chromophore does not absorb any UV light above 300 nm.

The following non-limiting examples illustrate certain aspects of the present invention. The examples first show the method for manufacturing the four components of the polymer system, the method for manufacturing the high refractive index silicone material from those components and the use of that high refractive index silicone material to make an intraocular lens.

Component I: Polyorganovinylsiloxanes (POS) of formula I are obtained by copolymerization of organosiloxanes of cyclic and/or linear structure in the presence of base catalysts. The POS composition is formed by copolymerization of a mixture of equal portions by mass of octaphenylcyclotetrasiloxane ($P_4$), octamethylcyclo-tetrasiloxane ($D_4$), and hexavinyldisiloxane (HVDS) in the presence of an active catalyst, such as hydroxides or alcoholates of alkaline metals or tetramethyl-ammonium, but preferably CsOH. This is a heterophase system and copolymerization of this mixture should be conducted at temperatures greater than about 150° C. The reaction yields a POS compound with a high content of diphenylsiloxy units. The products of the reaction are then neutralized using carbon dioxide, phosphorous acid or silyl phosphate. The resulting carbonates of alkaline metals are then removed from the POS by washing with water or filtration. Volatile fractions are removed from the POS by vacuum treatment at a reduced pressure of about 10–50 mm of Hg and a temperature of about 170° to 180° C. If explosive compounds, such as tetramethylammonium, are used, their dissociation products are removed, for example, by vacuum treatment. However, this treatment may be insufficient and the POS product should then be washed with water and treated using cation exchange. Use of thermostable catalysts has the advantage of producing a nearly optically clear product without filtration; however, use of the POS products in ophthalmology without filtration is not recommended.

The following are some specific examples of the synthesis of the component I POS materials:

COMPONENT I—EXAMPLE 1

62.4 g of $P_4$ (octaphenylcyclotetrasiloxane), 41.3g of $D_4$ (octamethylcyclotetra-siloxane), 2.32g of $V_4$ (tetramethylvinylcyclotetrasiloxane) and 1.86 g HVDS (hexavinyldisiloxane) are added to a 500 mL reactor, equipped with a stirrer, thermometer, and a means for continuous heating and cooling of the reaction mixture. While stirring, the reaction mixture is subsequently heated to about 140°–150° C. Once the temperature reaches about 140°–150° C., a small amount of a 40% solution of CsOH is added to the reaction mixture. The temperature is maintained at from about 140–150° C. for approximately 6 hours. The reaction mixture is then cooled to about 80°–110 ° C. and the CsOH neutralized by bubbling $CO_2$ into the reaction mixture. The POS reaction product is subsequently washed with deioinzed water (5x). The volatile components are distilled under reduced pressure (1 to 20 mm of Hg) at a temperature of 190° C. The physical and chemical characteristics and properties of the POS product are tabulated in Table 2 below.

COMPONENT I—EXAMPLE 2

In a manner analogous to that described in Example I-1, 58.7 g $P_4$, 39.4 g $D_4$, 1.45 g $V_4$ and 0.56 g HVDS are combined. The reaction mixture is polymerized through the addition of the CsOH catalyst. The resulting product is neutralized and washed as described in Example 1. The physical and chemical properties of the POS product are tabulated in Table 2 below.

COMPONENT I—EXAMPLE 3

In a manner analogous to Example I-1, 75.21 g $P_4$, 23.0 g $D_4$, and 1.79 g HVDS are combined and heated to about 140–150° C. Once the reaction temperature is about 140–150° C., a solution of the CsOH catalyst is added to the mixture. The reaction is subsequently neutralized with 0.02 g of an 85% solution of o-phosphoric acid. The reaction product is washed with deioinzed water (5x) and distilled under reduced pressure. The physical and chemical properties of the POS product are tabulated in Table 2 below.

COMPONENT I—EXAMPLE 4

Following the procedure described in Example I-1, 84.9 g $P_4$, 13.14 g $D_4$, 0.53 g $V_4$ and 1.43 g HVDS are co-polymerized by adding a solution of CsOH. The reaction mixture is subsequently neutralized, washed with deionized water, and distilled under reduced pressure. The physical and chemical properties of the POS product are tabulated in Table 2 below.

COMPONENT I—EXAMPLE 5

In a manner analogous to Example I-1, 86.0 g $P_4$, 13.77 g $D_4$, and 2.57 g divinyltetramethyldisiloxane (DVTMDS) are combined and co-polymerized by adding a solution of CsOH. The reaction mixture is then neutralized, washed, and distilled under reduced pressure. The physical and chemical properties of the POS product are tabulated in Table 2 below.

TABLE 2

Examples of Component I

| Example # | Indexes of formula I | | | | Molecular weight (MW) | Refractive Index ($nD^{20}$) | Content of Phenyl Groups (Mole %) | Content of Vinyl Groups (Mole %) | Ratio of C/Si | Bromine Number | Ratio of Phenyl/Si | Viscosity (cPs) |
|---|---|---|---|---|---|---|---|---|---|---|---|---|
| | m | n | k | x | | | | | | | | |
| I-1 | 0.62 | 0.35 | 0.03 | 90 | 10,784 | 1.525 | 45.0% | 2.20% | 2.37 | 12.90 | 1.92 | 35,000 |
| I-2 | 0.63 | 0.35 | 0.02 | 350 | 41,470 | 1.528 | 45.7% | 0.85% | 2.37 | 5.20 | 1.88 | 68,000 |
| I-3 | 0.45 | 0.55 | — | 90 | 13,032 | 1.568 | 58.5% | 1.24% | 3.20 | 7.40 | 2.95 | 120,000 |
| I-4 | 0.29 | 0.70 | 0.01 | 100 | 16,326 | 1.608 | 66.0% | 1.16% | 3.83 | 6.90 | 3.77 | 180,000 |
| I-5 | 0.30 | 0.70 | — | 450 | 72,546 | 1.610 | 66.9% | 0.07% | 3.87 | 0.44 | 3.83 | 380,000 |

Component II: Hydride oligomers are manufactured by hydrolysis of chlorosilane monomers followed by distillation. The following monomers can, for example, be used to achieve the desired value of refractive index and other properties for the vulcanized composition:

1. Dimethyldichlorosilane (DMDCS);
2. Methylhydridedichlorosilane (MHDCS);
3. Methylphenyldichlorosilane (MPDCS);
4. Phenyltrichlorosilane (PTCS);

5. Trimethylchlorosilane (TMCS);
6. Triphenylchlorosilane (TPCS);
7. Diphenyldichlorosilane (DPDCS);
8. Phenylhydridedichlorosilane (PHDCS)

The process of hydrolysis is typically carried out in the presence of aromatic solvents (such as tolulene or xylene) at a temperature of 60±5° C. in a volume of twice as much water by mass as the monomers. In order to achieve a consistent refractive index, the ratio of the monomers must be calculated with a high degree of accuracy. The products of the reaction are allowed to separate into an upper organic layer and a lower aqueous layer. The upper organic layer is removed and neutralized using $NaHCO_3$. The product is then washed with distilled water. The neutralized product should have a pH of about 6.8 to 7.0. Volatile components are then distilled from the product under a reduced pressure of about 5 to 20 mm of Hg.

The product is then subjected to a catalytic rearrangement (CR) in the presence of an ion exchange resin. The quantity of resin used is in the range of about 1.0 to 2.0 percent by weight. The CR is carried out for about 5 to 10 hours at a temperature of about 60° to 80° C. until a constant viscosity is achieved. The product is then separated from the resin by filtration and distilled to remove volatile fractions under a reduced pressure of about 1 to 3 mm of Hg and a distillation temperature of about 120° to 140° C. The process should yield greater than 99% by weight oligomer. The content of active hydrogen, refractive index, molecular weight, etc., are then measured to characterize the product.

COMPONENT II—EXAMPLE 1

In a 300 mL reactor equipped with stirrer, water jacket, thermometer, and dropping funnel, is added 32.81 g water and 8.20 g toluene. The reaction mixture is heated to about 60±5° C. While stirring, a mixture of 7.64 g MPDCS, 4.23 g PTCS, 3.45 g MHDCS, 1.08 g TMCS in 8.20 g toluene is added to the reaction mixture via an addition funnel. Subsequent to the addition, the reaction is stirred for an additional 1.0–1.5 h. At this point, stirring is stopped and the reaction mixture allowed to separate into two distinct layers (ca. 30 min.). The lower aqueous layer is drained off from the reaction mixture. The upper organic layer is neutralized with about 1.70–1.85 g $NaHCO_3$ and filtered to remove the remaining inorganic sediment (NaCl+redundant $NaHCO_3$). The product is purified by distillation under reduced pressure to remove volatile solvents.

The catalytic rearrangement (CR) is conducted in the presence of 1.5% by weight of an ion exchange resin at 70°–80° C. for 6 to 8 hours until a constant viscosity is achieved. The reaction mixture is subsequently filtered to remove the resin and distilled at 120° C.–140° C. under reduced pressure to remove any volatile components. The chemical and physical properties of the oligomer product are tabulated in Table 3 below.

COMPONENT II—EXAMPLE 2

In a manner analogous to that set forth in Example I-1, 15.18 g DPDCS, 3.45 g MHDCS, 1.08 g TMCS, 20 g of a 2:1 by weight mixture of toluene and butyl alcohol are combined. The resulting reaction products are neutralized, filtered, and distilled under reduced pressure. The catalytic rearrangement is conducted as described Example II-1. The chemical and physical properties of the oligomer product are tabulated in Table 3 below.

COMPONENT II—EXAMPLE 3

Following the process set forth in Example II-1, a mixture of 15.18 g DPDCS, 5.37 g PHDCS, 1.08 g TMCS and 20 g of the mixture of solvents as in Example II-2 are added to the reactor. After completion of the reaction, the products are neutralized, filtered, and distilled, and the catalytic rearrangement is conducted as in Example II-1. The chemical and physical properties of the oligomer product are tabulated in Table 3 below.

TABLE 3

| | Examples of Component II | | | | | | | | |
|---|---|---|---|---|---|---|---|---|---|
| Example # | Indexes of formula II | | | | Molecular weight (MW) | Refractive Index ($nD^{20}$) | Content of Phenyl Groups (Mole %) | Content of Si-H Bonds (Mole %) | Ratio of C/Si | Ratio of Phenyl/Si |
| | a | b | c | y | | | | | | |
| II-1 | 0.40 | 0.30 | 0.20 | 14 | 1,440 | 1.521 | 43.46% | 0.28% | 1.97 | 1.65 |
| II-2 | 0.60 | 0.30 | — | 17 | 2,464 | 1.562 | 63.77% | 0.21% | 3.34 | 3.30 |
| II-3 | 0.60 | 0.30 | — | 16 | 2,620 | 1.603 | 70.64% | 0.18% | 3.98 | 4.12 |

Component III: A second vulcanizing agent is used to reinforce the vulcanizate such that the mechanical properties of the final silicone material are optimized for use in an intraocular lens. These vinyl-containing oligomers are prepared by using vinyl-containing monomers, rather than the hydride-containing monomers used in the examples for Component II, and are modified "mirror" oligomers of the hydride vulcanizing agents described in formula II where the hydride groups are replaced by vinyl-containing groups. These "mirror" oligomers are identical in all other respects regardless of the hydride oligomer. This is clear when comparing formula II with formula III.

Vinyl-containing oligomers are manufactured by hydrolysis of chlorosilane monomers followed by distillation. The following monomers can, for example, be used to achieve the desired refractive index and other properties for the vulcanized composition:

1. Dimethyldichlorosi lane (DMDC S);
2. Methylvinyldichlorosilane (MVDCS);
3. Methylphenyldichlorosilane (MPDCS);
4. Phenyltrichlorosilane (PTCS);
5. Trimethylchlorosilane (TMCS);
6. Triphenylchlorosilane (TPCS);
7. Diphenyldichlorosilane (DPDCS);
8. Phenylvinyldichlorosilane (PVDCS)

The mole percentage content of vinyl units in Component III should relatively correspond to the mole percentage content of hydride units in Component II. This is important to assure that the refractive indices of the two components are relatively equal. As a rule, vinyl oligomers (Component III) are introduced into the mixture in lesser amounts, ranging from about 0.015 to about 0.05 weight parts, in comparison to the total quantity of POS (Component I) and hydride oligomer (Component II). This assures that no hydride groups are left as free radicals which could leach out reducing the biocompatibility of the final vulcanizate.

Examples of Component III are manufactured as described above for Component II except the hydride groups are replaced by vinyl groups. The chemical and physical properties of these materials are shown in Table 4.

TABLE 4

Examples of Component III

| Example # | Indexes of formula III | | | | Molecular weight (MW) | Refractive Index ($nD^{20}$) | Content of Phenyl Groups (Mole %) | Content of Vinyl Bonds (Mole %) | Ratio of C/Si | Ratio of Phenyl/Si |
|---|---|---|---|---|---|---|---|---|---|---|
| | a | b | c | y | | | | | | |
| III-1 | 0.40 | 0.30 | 0.20 | 12 | 1,483 | 1.520 | 40.49% | 2.10% | 2.23 | 1.65 |
| III-2 | 0.60 | 0.30 | — | 18 | 2,901 | 1.562 | 60.51% | 5.30% | 3.00 | 3.20 |
| III-3 | 0.60 | 0.30 | — | 14 | 2,398 | 1.597 | 67.42% | 4.73% | 4.24 | 4.12 |

Component IV Catalysts: A complex platinum catalyst is used in these compositions because of its proven biocompatibility. A preferred catalyst is obtained by the reaction of $H_2PtCl_6 \cdot 6H_2O$ and tetravinyldimethyldisiloxane (V-2) or hexavinyldisiloxane (V-6).

Filtration of the Four Components: To assure optical clarity, each of the four finished polymer components may be filtered using a 0.22 μm porous filter (Catalog ASWP 14250 LON H7E82220 B, filter type GS, Pore size 0.22 um., Millipore Corporation). Filtration is preferably carried out at a differential pressure of about 2 to 3 atmospheres.

Molding of the Intraocular Lens (IOL): Preparation of the finished composition may be completed by simply mixing the appropriate portions of the individual components, removing air bubbles (for example, using a vacuum), molding in an appropriate mold, heating to a temperature of about 110° to 150° C., and holding at that temperature for about 2 to 10 minutes. Examples of the formulation of IOL's of the present invention are set forth below.

PREPARATION OF AN IOL—EXAMPLE 1

To a 100 mL reactor equipped with stirrer, water jacket and vacuum system, is added 12.00 g of the POS of Example I-1, 1.35 g of the hydride oligomer of Example II-1, 0.15 g of the vinyl oligomer of Example III-1, and 0.001 g of the complex catalyst V-6. The mixture is stirred at a temperature of about 35°–37° C., and under a reduced pressure of about 1–3 mm of Hg, for 5–10 minutes. Any air bubbles in the composition are removed and an IOL mold is filled with the composition and vulcanized at about 110° to 150° C. for fabrication of the IOL. The optical and mechanical properties of the vulcanizate are shown in Table 5.

PREPARATION OF AN IOL—EXAMPLE 2

Using a method similar to IOL Example IOL-1, 13.50 g of the POS of Example I-2, 1.35 g of hydride oligomer Example II-2, 0.15 g of the corresponding vinyl oligomer of Example III-2, and 0.001 g of the complex catalyst V-2 are combined. Any air bubbles in the composition are removed and an IOL mold is filled with the composition and vulcanized at about 110° to 150° C., under a reduced pressure of about 1–3 mm Hg, for 5–10 minutes. The optical and mechanical properties of the vulcanizate are shown in Table 5.

PREPARATION OF AN IOL—EXAMPLE 3

Using a method similar to IOL Example 1, 14.25 g of the POS of Example I-3, 0.675 g of the hydride oligomer of Example II-2, 0.075 g of the corresponding vinyl oligomer of Example III-2, and 0.002 g of the complex catalyst V-2 are combined. Any air bubbles in the composition are removed and an IOL mold is filled with the composition and vulcanized at about 110° to 150° C., under a reduced pressure of about 1–3 mm Hg, for 5–10 minutes. The optical and mechanical properties of the vulcanizate are shown in Table 5.

PREPARATION OF AN IOL—EXAMPLE 4

Using a method similar to Example 1, mix 14.40 g of the POS of Example I-4, 1.12 g of the hydride oligomer of Example II-4, 0.15 g of the corresponding vinyl oligomer of Example III-4, and 0.0015 g of the complex catalyst V-2. Extract air bubbles and fill the IOL mold with the mixed composition, vulcanize at 110° to 150° vacuum of 1–3 mm Hg, for 5–10 minutes, to fabricate the IOL. The optical and mechanical properties of the vulcanizate are shown in Table 5.

TABLE 5

IOL Examples

| IOL Example # | Refractive Index ($nD^{20}$) | Tensile Strength ($Kg/cm^2$) | Content of Phenyl Groups (Mole %) | Elongation (%) | UV Light Absorbance (%) |
|---|---|---|---|---|---|
| 1 | 1.524 | 29.6 | 45% | 107% | 60% |
| 2 | 1.525 | 28.1 | 46% | 126% | 62% |
| 3 | 1.564 | 12.1 | 58% | 179% | 68% |
| 4 | 1.605 | 7.8 | 65% | 192% | 78% |

The current invention reinforces the silicone material to provide excellent mechanical properties while permitting a high concentration of phenyl groups by using mirrored hydride and vinyl-containing vulcanizing or cross-linking components. The vulcanization reaction is very easy to control.

While the current invention has been described with respect to various specific examples and embodiments, it is to be understood that the invention is not limited thereto and that it can be variously practiced within the scope of the following claims.

What is claimed is:

1. An intraocular lens having a refractive index of at least about 1.50, made from an optically-clear silicone material having a content of phenyl groups of at least about 35 mole %, which is formed by the vulcanization of the mixture which comprises:

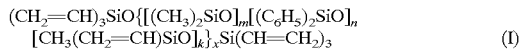  (I)

wherein m+n+k=1, m is from about 0.5 to about 0.7, n is from about 0.3 to about 0.5, k is from about 0.01 to about 0.02, and x is from about 350 to about 450;

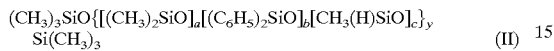  (II)

wherein a+b+c=1, a is from about 0.4 to about 0.5, b is from about 0.2 to about 0.4, c is from about 0.02 to about 0.04, and y is from about 5 to about 10; and

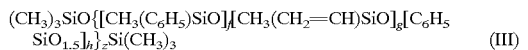  (III)

wherein f+g+h=1, f is from about 0.3 to about 0.4, g is from about 0.2 to about 0.4, h is from about 0.01 to about 0.04, and z is from about 7 to about 10; said vulcanization taking place in the presence of a polyaddition reaction catalyst.

2. An intraocular lens according to claim 1 wherein the mixture which is vulcanized to form the silicone material which contains from about 0.7 to about 0.9 parts by weight component (I), from about 0.1 to about 0.3 parts by weight component (II), and from about 0.015 to about 0.05 parts by weight component (III).

3. An intraocular lens according to claim 1 wherein the polyaddition reaction catalyst is a complex of platinum with hexavinyldisiloxane and is present in a catalytically effective amount.

4. An intraocular lens according to claim 3 wherein the mixture which is vulcanized to form the silicone material which contains from about 0.006 parts by weight to about 0.01 parts by weight of the reaction catalyst.

5. An intraocular lens according to claim 2 wherein the vulcanized silicone material has a content of phenyl groups of at least about 45 mole %.

6. An intraocular lens according to claim 5 having a refractive index of at least about 1.52.

7. An intraocular lens according to claim 5 wherein the vulcanized material has a content of phenyl groups of from about 45 mole % to about 65 mole %.

8. An intraocular lens having a refractive index of at least about 1.50, made from an optically-clear silicone material having a content of phenyl groups of at least about 35 mole %, which is formed by the vulcanization of a mixture which comprises:

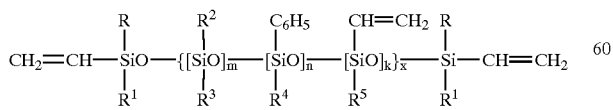  (I)

wherein m+n+k=1; m is from about 0.29 to about 0.70; n is from about 0.30 to about 0.70; k is from 0 to about 0.03; x is from about 90 to about 450; R and $R^1$ are selected from $C_1$–$C_4$ alkyl, $C_1$–$C_4$ alkenyl and $C_6H_5$; $R^2$ and $R^3$ are selected from $C_1$–$C_4$ alkyl; $R^4$ is selected from $C_1$–$C_4$ alkyl and $C_6H_5$; $R^5$ is selected from $C_1$–$C_4$ alkyl and $C_6H_5$;

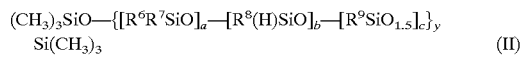  (II)

wherein a+b+c=1; a is from about 0.2 to about 0.7; b is from about 0.2 to about 0.4; c is from about 0.01 to about 0.04; y is from about 5 to about 22; $R^6$ is selected from $C_1$–$C_4$ alkyl and $C_6H_5$, $R^7$ is selected from $C_1$–$C_4$ alkyl and $C_6H_5$; $R^8$ is selected from $C_1$–$C_4$ alkyl and $C_6H_5$; $R^9$ is selected from $C_1$–$C_4$ alkyl and $C_6H_5$;

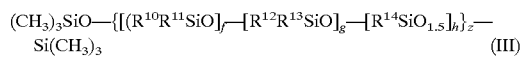  (III)

wherein f+g+h 1; f is from about 0.2 to about 0.7; g is from about 0.2 to about 0.4; h is from about 0.01 to about 0.03; z is from about 10 to about 22; $R^{10}$, $R^{11}$, and $R^{12}$ are selected from $C_1$–$C_4$ alkyl and $C_6H_5$; $R^{13}$ is (CH=CH$_2$); and $R^{14}$ is selected from $C_1$–$C_4$ alkyl, $C_1$–$C_4$ alkenyl and $C_6H_5$; and said vulcanization taking place in the presence of a polyaddition reaction catalyst.

9. An intraocular lens according to claim 8 wherein R is CH=CH$_2$; $R^1$ is CH=CH$_2$; $R^2$ is CH$_3$; $R^3$ is CH$_3$; $R^4$ is $C_6H_5$, $R^5$ is CH$_3$, $R^6$ is selected from CH$_3$ and $C_6H_5$; $R^7$ is $C_6H_5$; $R^8$ is selected from CH$_3$ and $C_6H_5$; $R^9$ is $C_6H_5$; $R^{10}$ is selected from CH$_3$ and $C_6H_5$; $R^{11}$ is $C_6H_5$; $R_{12}$ is selected from CH$_3$ and $C_6H_5$, $R^{13}$ is CH=CH$_2$; and $R^{14}$ is CH=CH$_2$.

10. An intraocular lens according to claim 8 wherein the mixture which is vulcanized to form the silicone material which contains from about 0.7 to about 0.9 parts by weight component (I), from about 0.1 to about 0.3 parts by weight component (II), and from about 0.015 to about 0.05 parts by weight component (III).

11. An intraocular lens according to claim 8 wherein the polyaddition reaction catalyst is a complex of platinum with hexavinylsiloxane and is present in a catalytically effective amount.

12. An intraocular lens according to claim 11 wherein the mixture which is vulcanized to from the silicone material which contains from about 0.006 to about 0.01 parts by weight of the reaction catalyst.

13. An intraocular lens according to claim 8 wherein

Component (I) is α, ω-bis (trivinylsiloxy) oligodimethyldiphenyl-vinylmethylsiloxane; and Component (III) is α, ω-bis (trimethylsiloxy) oligomethylphenyl-vinylmethylphenylsiloxane.

* * * * *